(12) United States Patent
Bouduban et al.

(10) Patent No.: US 10,058,366 B2
(45) Date of Patent: Aug. 28, 2018

(54) SURGICAL IMPLANT

(71) Applicant: CC Innovation, Innsbruck (AT)

(72) Inventors: Nicolas Bouduban, Oberdorf (CH);
Beat Lechmann, Oberdorf (CH);
Patrick Burki, Oberdorf (CH);
Christian Fink, Innsbruck (AT)

(73) Assignee: CC Innovation, Innsbruck (AT)

( * ) Notice: Subject to any disclaimer, the term of this patent is extended or adjusted under 35 U.S.C. 154(b) by 0 days.

(21) Appl. No.: 15/233,153

(22) Filed: Aug. 10, 2016

(65) Prior Publication Data

US 2016/0346023 A1    Dec. 1, 2016

Related U.S. Application Data (62) Division of application No. 13/282,094, filed on Oct. 26, 2011, now Pat. No. 9,839,458.

(Continued)

(51) Int. Cl.
*A61B 17/84*    (2006.01)
*A61B 17/92*    (2006.01)
(Continued)

(52) U.S. Cl.
CPC ........ *A61B 17/844* (2013.01); *A61B 17/0642* (2013.01); *A61B 17/0682* (2013.01);
(Continued)

(58) Field of Classification Search
CPC ............. A61B 17/064; A61B 17/0642; A61B 17/0643; A61B 17/076; A61B 17/0644; A61B 17/0641; A61B 17/0645; A61B 17/0646; A61B 2017/00646; A61B 2017/00668; A61B 17/92; A61B 2017/922; A61B 2017/925; B25D 1/16
(Continued)

(56) References Cited

U.S. PATENT DOCUMENTS 3,787,608 A    1/1974   Colby et al.
3,894,174 A    7/1975   Cartun
(Continued)

FOREIGN PATENT DOCUMENTS

CN    1148796    4/1997
CN    1907238    2/2007
(Continued)

OTHER PUBLICATIONS

Japan Office Notice of Reason for Preliminary Rejection (JP2013-540651).
(Continued)

*Primary Examiner* — Todd E Manahan
*Assistant Examiner* — Marcela I Shirsat
(74) *Attorney, Agent, or Firm* — Meunier Carlin & Curfman LLC (57) ABSTRACT

A surgical implant for fixing a soft tissue to a bone comprising a staple and a plate. The staple and the plate are positionable on an instrument in such a way that the plate may be manipulated with the instrument to hold the soft tissue against the bone and in such a way that the staple is fixable to the bone with the plate positioned between a bridge of the staple and the soft tissue when legs of the staple are driven through the plate and into the bone.

10 Claims, 7 Drawing Sheets

Related U.S. Application Data (60) Provisional application No. 61/416,668, filed on Nov. 23, 2010.

(51) Int. Cl.
*A61B 17/068* (2006.01)
*A61F 2/08* (2006.01)
*A61B 17/064* (2006.01)
*A61B 17/00* (2006.01)
*B25D 1/16* (2006.01)

(52) U.S. Cl.
CPC ............ *A61B 17/92* (2013.01); *A61F 2/0805* (2013.01); *A61F 2/0811* (2013.01); *A61B 17/064* (2013.01); *A61B 17/0643* (2013.01); *A61B 17/0644* (2013.01); *A61B 2017/00668* (2013.01); *A61B 2017/0641* (2013.01); *A61F 2002/0823* (2013.01); *A61F 2002/0858* (2013.01); *A61F 2002/0888* (2013.01); *B25D 1/16* (2013.01)

(58) Field of Classification Search
USPC ....... 606/71, 75–76, 78, 151, 219, 280, 297, 606/286, 300, 311, 324, 326–327, 329, 606/330–331, 120, 157, 158, 213, 215, 606/216, 220–222; 128/831, 834; 411/469, 474; 227/175.1–182.1, 227/901–902, 110; 81/463
See application file for complete search history.

(56) References Cited

U.S. PATENT DOCUMENTS

| | | | |
|---|---|---|---|
| 4,278,091 A | 7/1981 | Borzone | |
| 4,462,395 A | 7/1984 | Johnson | |
| 4,988,351 A | 1/1991 | Paulos et al. | |
| 5,209,756 A | 5/1993 | Seedhom et al. | |
| 5,258,012 A | 11/1993 | Luscombe et al. | |
| 5,352,229 A | 10/1994 | Goble et al. | |
| 5,425,490 A | 6/1995 | Goble et al. | |
| 5,779,707 A | 7/1998 | Bertholet et al. | |
| 6,325,805 B1 | 12/2001 | Ogilvie et al. | |
| 6,582,452 B2* | 6/2003 | Coleman | A61B 17/0057 227/175.1 |
| 6,709,439 B2* | 3/2004 | Rogers | A61B 17/88 606/100 |
| 6,712,822 B2 | 3/2004 | Re et al. | |
| 7,008,435 B2* | 3/2006 | Cummins | A61B 17/0057 606/139 |
| 8,348,972 B2 | 1/2013 | Soltz et al. | |
| 2004/0073222 A1* | 4/2004 | Koseki | A61B 17/0642 606/75 |
| 2005/0250379 A1 | 11/2005 | Coffey | |
| 2010/0063506 A1 | 3/2010 | Fox et al. | |
| 2010/0217393 A1 | 8/2010 | Theofilos | |

FOREIGN PATENT DOCUMENTS

| | | |
|---|---|---|
| CN | 101448465 | 6/2009 |
| EP | 0 624 350 | 11/1994 |
| EP | 0 768 062 | 4/1997 |
| JP | 05-502803 | 5/1993 |
| JP | 06-327697 | 11/1994 |
| JP | 2005-528927 | 9/2005 |
| WO | 91/06249 | 5/1991 |
| WO | 98/37825 | 9/1998 |

OTHER PUBLICATIONS

International Search Report and Written Opinion (PCT/US2011/057885); dated May 16, 2012.
Chinese Office Action (CN201180051758.2); dated Dec. 17, 2014.
Non-Final Office Action issued in U.S. Appl. No. 15/787,323, dated Apr. 5, 2018.

* cited by examiner

SURGICAL IMPLANT

CROSS REFERENCE TO RELATED APPLICATIONS

The present application is a divisional of U.S. Ser. No. 13/282,094, filed Oct. 26, 2011, which claims benefit of U.S. Provisional Ser. No. 61/416,668, filed Nov. 23, 2010, each of which being hereby incorporated herein by reference in its entirety.

BACKGROUND OF THE INVENTION

The inventive concepts disclosed herein generally relate to a surgical implant. More particularly, the inventive concepts relate to a surgical implant for attaching soft tissue, ligaments or tendons to bone. Embodiments of the invention relate to a method for attaching soft tissue, ligaments or tendons to bone, to an instrument for implanting a surgical implant according to the invention into a body portion of a patient and to a kit for attaching soft tissue, ligaments or tendons to bone comprising an instrument and one or more surgical implants.

BRIEF SUMMARY OF THE INVENTION

An object of the inventive concepts disclosed herein is to provide a surgical implant allowing soft tissue, such as a ligament or a tendon, to be positioned and held on the surface of a bone before finally affixing the soft tissue to the bone.

The inventive concepts disclosed herein relate to a surgical implant comprising: a staple with two or more legs connected by a bridge, the staple comprising a material having a tensile strength TS1; and a plate with an upper side and a lower side, and wherein the staple is fixable to a bone with the bridge extending over the plate.

In one embodiment, the legs of the staple can pass through perforations of the plate. The plate can thus be firmly held in its lateral position by the legs of the staple.

The surgical implant according to the inventive concepts disclosed herein allows a temporary fixation of the soft tissue by means of the plate and that after a possible correction or adaptation of the position of the soft tissue the final fixation can be performed by pushing the staple through or over the temporarily fixed plate.

The surgical implant according to the inventive concepts disclosed herein is a simple and versatile implant for the fixation of soft tissue tears and allows better soft tissue repositioning and better bony fixation.

In another embodiment, the plate comprises a material having a tensile strength TS2<TS1 so that the plate may be perforated from its upper side to its lower side by the legs of the staple. This configuration allows the advantage that the plate can be configured without perforations and can be perforated from its upper side to its lower side by the legs of the staple upon impaction of the staple.

In a further embodiment, the plate has a number of blind holes or through-going perforations arranged with the same geometry as the legs of the staple. This configuration allows an easier impaction of the staple through the plate. If the plate comprises through-going perforations, the plate can consist of the same material as the staple. If the plate comprises blind holes, the plate can be easier perforated by the legs of the staple so that the insertion of the staple is facilitated. The through-going perforations or blind holes can have a cross sectional area which is smaller or equal to the cross sectional area of the legs of the staple so that the plate is prevented from a lateral movement relative to the staple. Alternatively, the through-going perforations or blind holes can have a cross sectional area which is larger than the cross sectional area of the legs of the staple thus allowing a clearance between the legs of the staple and the through-going perforations.

In a further embodiment of the surgical implant, the tensile strength TS1 is comprised in a range of from about 500 MPa to about 3300 MPa.

In another embodiment of the surgical implant, the tensile strength TS2 is comprised in a range of from about 60 MPa to about 200 MPa.

In another embodiment of the surgical implant, the material having a tensile strength TS1 is a metal or a metal alloy in particular stainless steel, titanium alloys, Co Cr alloys and magnesium-based metals.

In a further embodiment of the surgical implant, the material having a tensile strength TS2 is a non-resorbable plastic material, preferably chosen from the group of PAEK materials, polyethylene (PE) and polymethylmethacrylate (PMMA). An exemplary material is PEEK.

In a further embodiment of the surgical implant, the material having a tensile strength TS2 is a resorbable plastic material, such as PLLA, PLDLA, PLGA, or PCL.

In again a further embodiment of the surgical implant, the lower side of the plate has a roughened or three-dimensionally structure surface, such as a plurality of pyramid shaped teeth.

In yet a further embodiment of the surgical implant, the plate has a central hole. This central hole allows attachment of the plate to the front end of the sleeve of the instrument. The central hole may have a slightly smaller diameter than the front end or alternatively can be shaped conically to be frictionally received over the front end.

In another embodiment of the surgical implant, the legs have tapering ends which may be acuminated.

In another embodiment of the surgical implant, the legs have a roughened or three-dimensional structure, such as a saw-toothing.

In again another embodiment, the number of the legs may be three or four.

In yet another embodiment of the surgical implant, the plate has a recess in its upper side for receiving the bridge of the staple. The recess may be configured and dimensioned to match the bridge of the staple. This configuration allows the advantage that the plate is retained in its position relative to the staple so that soft tissue, such as a ligament or tendon, can be firmly fixed to a bone. Alternatively, the recess may have a cross sectional area which is larger than the cross sectional area of the bridge of the staple so that the bridge is received within the recess with a lateral clearance.

In still another embodiment of the surgical implant, the plate has a central axis orthogonal to the lower side and further comprises one or more channels that are open towards the upper side of the plate and extend across the plate orthogonally to the central axis. The channels facilitate cutting through the plate and bridge combination and thus facilitate an explantation of the surgical implant.

In a further embodiment, the plate is configured and dimensioned so that the staple engages the plate after fixation of the surgical implant to a bone, preferably with the legs laterally contacting the plate. The plate can comprise cutouts arranged, e.g., in the corners so that the legs of the staple can be partly received therein. The plate can thus be firmly held in its lateral position by the legs of the staple.

Alternatively, the legs of the staple can be arranged so that a small spacing remains between the legs and the periphery of the plate.

According to a further aspect of the inventive concepts disclosed herein, there is provided a method for attaching soft tissue, such as ligaments or tendons, to bone comprising the following steps:

fixing the soft tissue to the bone surface by pressing a plate with its lower side against the bone;

impacting a staple with its legs through or beside the plate from its free upper side so that the legs are anchored in the bone beneath the plate and the soft tissue is clamped between the plate and the bone.

In accordance with another aspect, an instrument for implanting a surgical implant into a body portion of a patient is provided comprising a longitudinal axis and coaxially arranged thereto: a sleeve having a front end with means for releasably fixing a plate thereto; an impact rod slideably arranged in the sleeve; an impact block that is affixed to the impact rod and slideably arranged on the outer peripheral surface of the sleeve and that comprises means for releasably fixing a staple thereto in such a way that the legs of the staple are directed towards the front end of the sleeve.

In a further embodiment of the instrument, the staple of the surgical implant is attached to the impact block and the plate of the surgical implant is attached to the front end of the sleeve and wherein the staple and the plate are positioned coaxially to each other.

In accordance with again another aspect, a kit is provided for attaching soft tissue, such as ligaments or tendons, to bone comprising an instrument according to the inventive concepts disclosed herein and one or more surgical implants according to the inventive concepts disclosed herein.

DETAILED DESCRIPTION OF EXEMPLARY EMBODIMENTS

Before explaining at least one embodiment of the inventive concepts in detail, it is to be understood that the inventive concepts disclosed herein are not limited in its application to the details of construction, experiments, exemplary data, and the arrangement of the components set forth in the following description or illustrated in the drawings. The inventive concepts are capable of other embodiments or being practiced or carried out in various ways. Also, it is to be understood that the phraseology and terminology employed herein is for purposes of description and should not be regarded as limiting.

Figure 1:
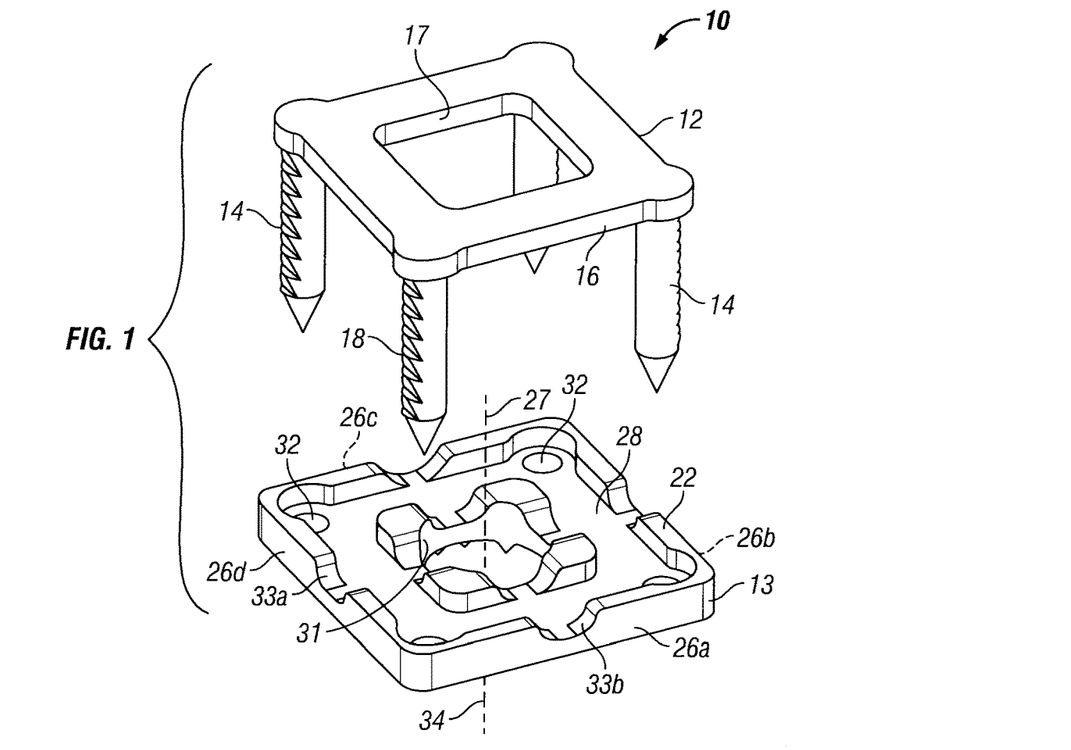
FIG. 1 is a perspective view of an embodiment of a surgical implant constructed in accordance with the inventive concepts disclosed herein illustrating a staple and a plate separated relationship to one another.
Figure 2:
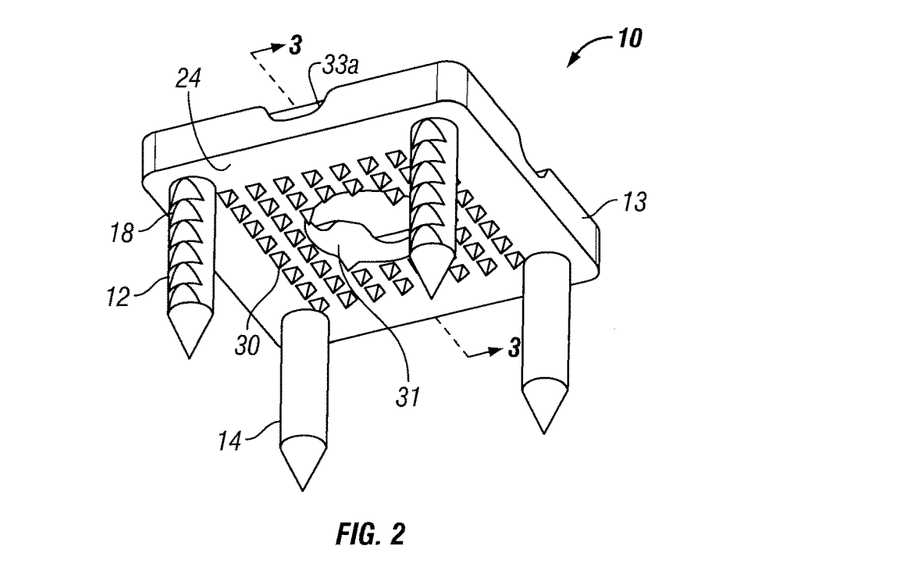
FIG. 2 is a lower perspective view of the surgical implant of FIG. 1 showing the staple impacted through the plate.
Figure 3:
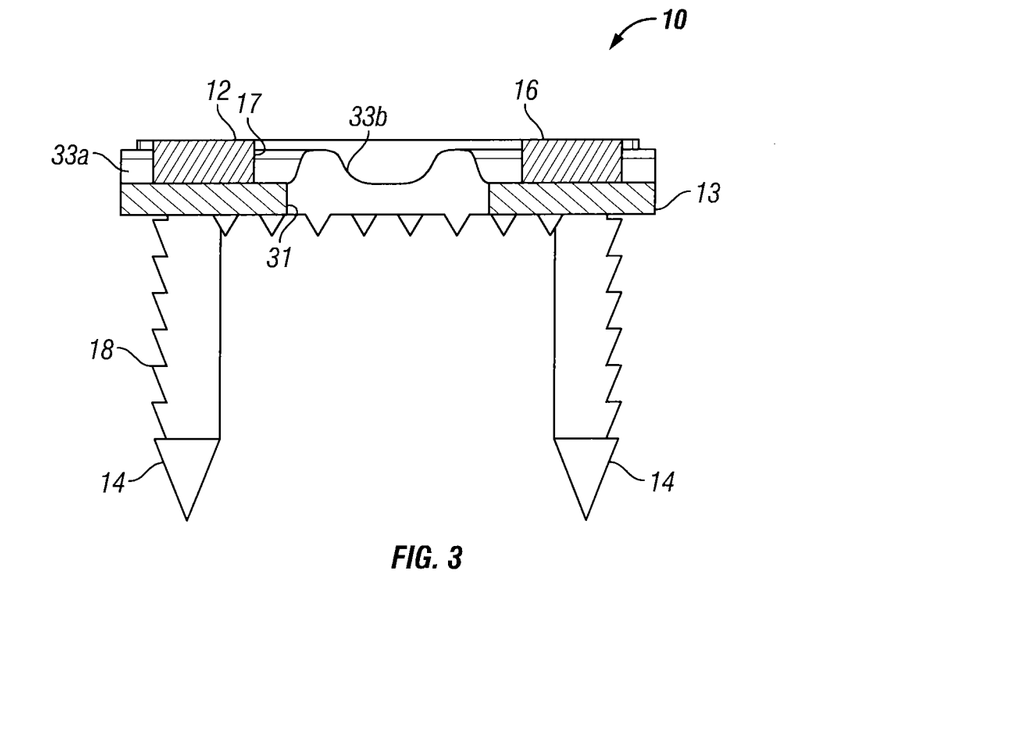
FIG. 3 is a cross sectional view taken along line 3-3 of FIG. 2.

Referring now to the drawings, and more particularly to FIGS. 1-3, one embodiment of a surgical implant 10 constructed in accordance with the inventive concepts disclosed herein is illustrated. Broadly, the surgical implant 10 includes a staple 12 and a plate 13.

The staple 12 is illustrated as having four legs 14 connected by a bridge 16 that may be formed in the shape of a generally square frame. It should be appreciated, however, that the number of legs 14 may be varied, as well as the shape of the bridge 16. For example, two or more legs may be utilized, and the bridge 16 may be formed to have any geometric, non-geometric, asymmetrical, or fancy design. For example, the bridge 16 may be formed as a rectangle, circle (FIG. 4), triangle, or octagon, or other forms such as stars or hearts. The bridge 16 has a central opening 17 for receiving a portion of an instrument in a manner to be described below. Each of the legs 14 is affixed to one corner of the bridge 16. The legs 14 are parallel to one another and extend perpendicular from the bottom side of the bridge 16. The free ends of the legs 14 are may be acuminated, and the legs 14 may be circular cylindrically configured. Each leg 14 may comprise a three-dimensional structure, such as a saw-toothing 18. In one embodiment, the saw-toothing 18 is located on each leg 14 at a side facing the outer periphery of the bridge 16. Further, the steep flanks of the saw-toothing 18 are directed towards the fixed end of each leg 14. The staple 12 can be formed of any suitable material such as a 652 L stainless steel with a tensile strength TS1.

Figures 4, 5:
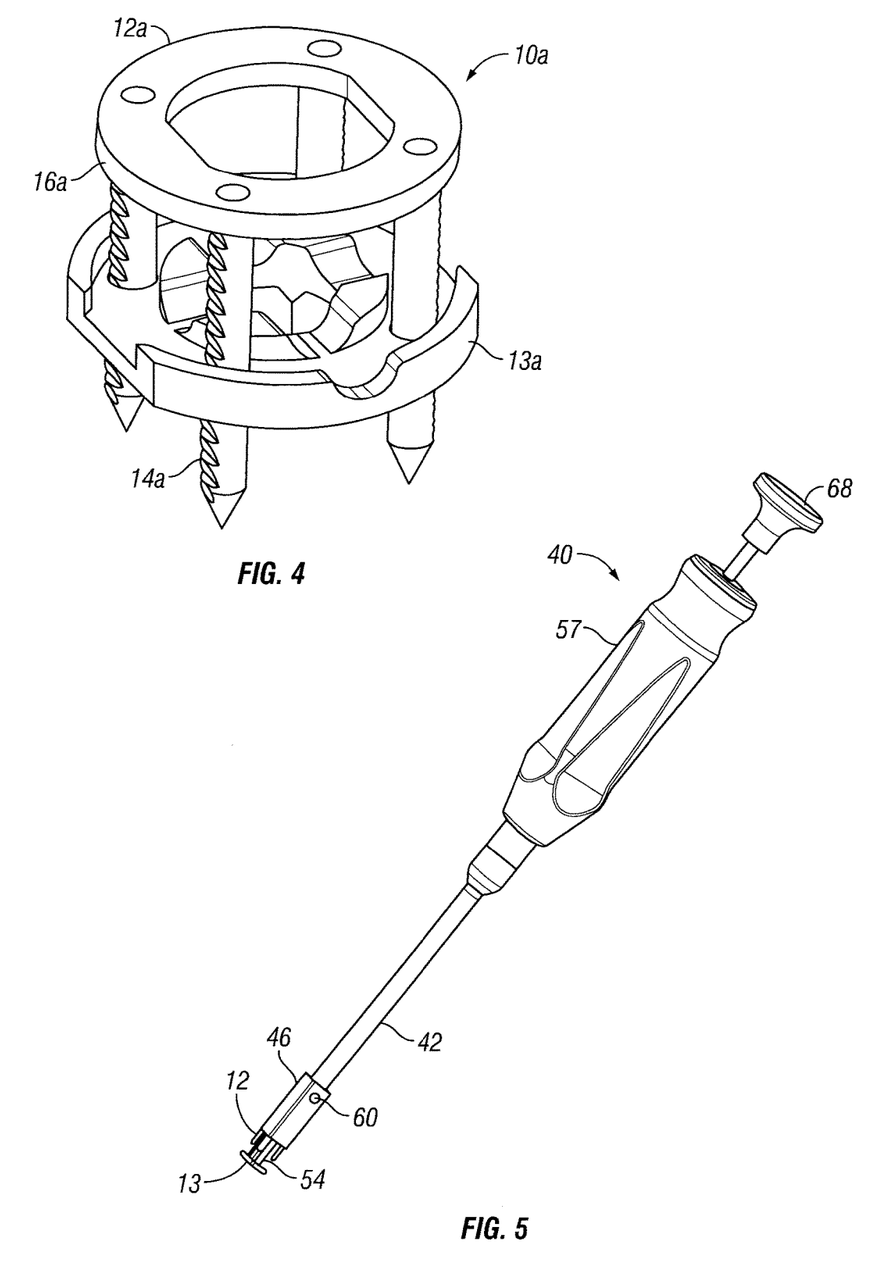
FIG. 4 is an upper perspective view of another embodiment of a surgical implant.
FIG. 5 is a perspective view of an embodiment of an instrument according to the inventive concepts disclosed herein.

In one embodiment, the plate 13 may have a generally square shape with an upper side 22, a lower side 24, four lateral sides 26a, 26b, 26c, and 26d and a central axis 27 orthogonal to the lower side 24. Like the bridge 16 of the staple 12 discussed above, the plate 13 may be formed to have a variety of shapes. By way of example, FIG. 4 illustrates another embodiment of a surgical implant 10a. The surgical implant 10a includes a staple 12a and a plate 13a. The staple 12a has a plurality of legs 14a and a bridge 16a. The bridge 16a and the plate 13a are substantially similar in construction and function to the bridge 16 and the plate 13 except that the bridge 16a and the plate 13a have a generally circular shape.

Returning now to FIGS. 1-3, the upper side 22 of the plate 13 has a recess 28. The recess 28 of the plate 13 is configured and dimensioned to matingly receive the bridge 16 of the staple 12. The lower side 24 of the plate 13 is preferably provided with a three-dimensional structural surface, such as a plurality of pyramid shaped teeth 30. The plate 13 has a central hole 31 extending through the plate 13 from the upper side 22 to the lower side 24 for receiving a portion of an instrument in a manner to be described below.

The plate 13 is further provided with a plurality of perforations 32 for receiving the legs 14 of the staple 12. Each of the perforations 32 is located in one corner of the recess 28 that is configured to receive the bridge 16 of the staple 12. When the staple 12 is implanted, the legs 14 of the staple 12 are driven through the perforations 32 in the plate 13 and into the bone until the bridge 16 abuts the surface of the recess 28 so that both the staple 12 and the plate 13 are fixed to the bone. The plate 13 can consist of the same material as the staple 12, which in one embodiment is a 652 L stainless steel.

Figure 3A:
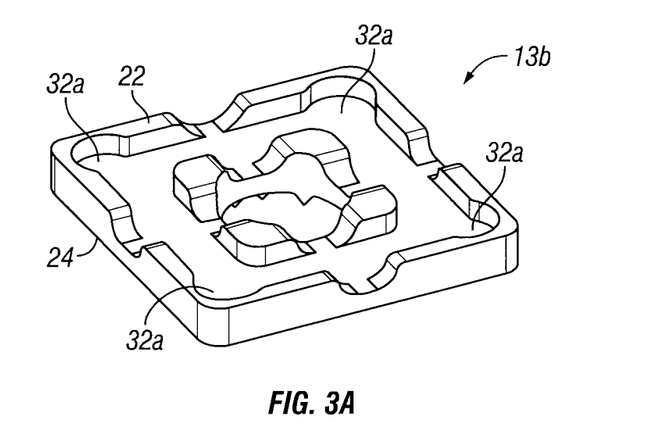
FIG. 3A is a perspective view of another embodiment of a plate according to the inventive concepts disclosed herein.

Alternatively, the plate 13 may be constructed of a material having a tensile strength TS2 which is less that the tensile strength TS1 of the staple 12. To this end, FIG. 3A illustrates another embodiment of a plate 13b. The plate 13b is similar to the plate 13 except that the plate 13b is formed without the perforations 32. In contrast, the plate 13b is provided with a plurality of blind holes 32b which can be perforated by the staple 12 upon impaction of the staple 12.

Alternatively, the plate 13 can be configured and dimensioned so that the staple 12 embraces the plate 13 after fixation of the surgical implant 10 to a bone. The legs 14 of the staple 12 can laterally contact the plate 13 or can have a small spacing to the periphery of the plate 13. In another embodiment, the plate 13 can be provided with four cutouts or notches for receiving the legs 14 of the staple 12 wherein the cutouts can be arranged in the corners or sides of the plate 13.

The recess 28 is preferably configured to match the bridge 16 of the staple 12, allowing mating engagement between the plate 13 and the staple 12. Alternatively, the perforations 32 can have a diameter allowing the legs 14 of the staple 12 to slideably penetrate through the perforations 32 upon insertion of the staple 12 so that the plate 13 is fixed by the legs 14 of the staple 12 against a lateral movement relative to the staple 12. As will be understood by those skilled in the art, the plate 13 can be laterally fixed via the staple 12 anchored in a bone either by means of a positive locking, if the bridge 16 of the staple 12 matches the recess 28 in the plate 13, and/or the legs 14 match the perforations 32, or by means of a frictional engagement if the bridge 16 of the staple 12 is received in the recess 28 with a clearance and if the legs 14 have a clearance within the perforations 32, or if the legs 14 of the staple 12 are arranged with a small spacing to the periphery of the plate 13.

Figure 6:
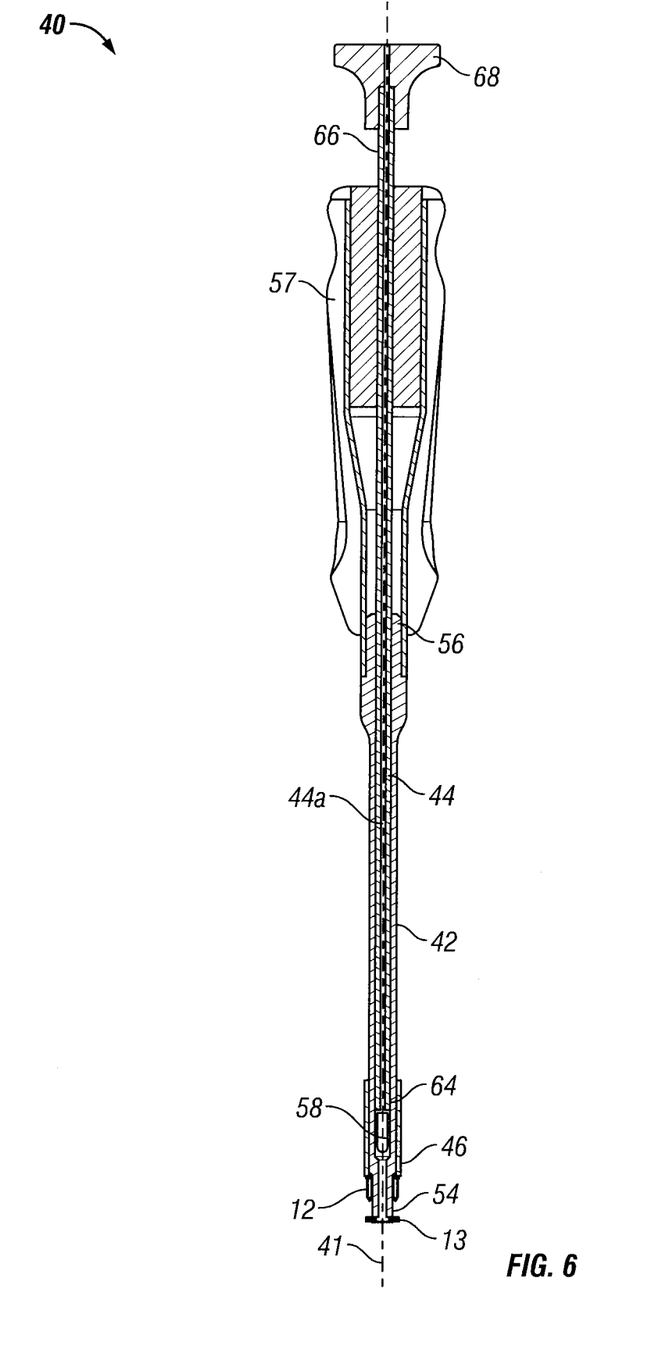
FIG. 6 is a longitudinal sectional view of the instrument shown in FIG. 5.
Figure 7:
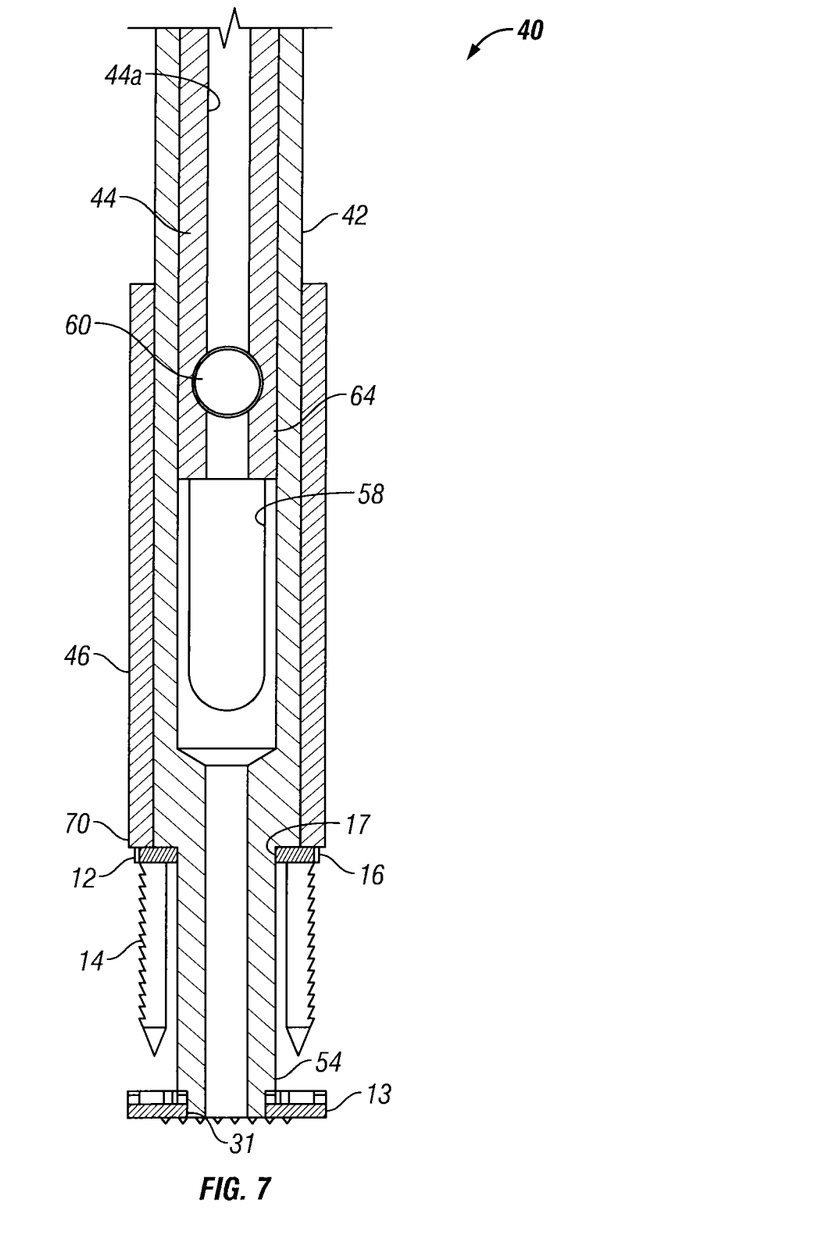
FIG. 7 is an enlarged sectional view of a portion of the instrument illustrated in a retracted position with the surgical implant positioned thereon.

The central hole 31 of the plate 13 allows for the attachment of the plate 13 to a front end of an instrument in a manner to be described below in reference to FIGS. 5-7. As such, the central hole 31 can be formed to have a variety of shapes, such as circular cylindrical, so long as the plate 13 can be attached to the front end of the instrument. Alternatively, the central hole 31 in the plate 13 can have a slightly smaller diameter than the front end of the instrument or the central hole 31 in the plate 13 can be shaped conically to receive and clamp on an instrument.

Furthermore, the plate 13 may be provided with a first and a second channel 33a and 33b which penetrate through the plate 13 orthogonally to a central axis 34. The first and second channels 33a and 33b are open towards the upper side 22 of the plate 13 so as to define cut lines to facilitate explantation of the staple 12 and the plate 13.

FIGS. 5-9 illustrate an embodiment of an instrument 40 for attaching soft tissue, such as ligaments and tendons, to bone using the surgical implant 10. The instrument 40 comprises a longitudinal axis 41 and coaxially arranged thereto a sleeve 42, an impact rod 44 slideably arranged in the sleeve 42, and an impact block 46 affixed to the impact rod 44 and slideably arranged on the outer peripheral surface of the sleeve 42. The impact rod 44 can be displaced in the sleeve 42 from a retracted position (FIGS. 5-8) where the staple 12 and the plate 13 are in a separated insertion position to an extended position (FIG. 9) where the legs 14 of the staple 12 are caused to penetrate through the plate 13 and into the bone. The impact rod 44 comprises a central passageway 44a so that the instrument 40 can be pushed over a Kirschner-wire (not shown). The sleeve 42 of the instrument 40 has a front end 54, a rear end 56, and a handle 57. Axially spaced apart from the front end 54, the sleeve 42 comprises two diametrically oppositely arranged slots 58 (only one of the slots 58 being visible in FIGS. 6 and 7) extending along the longitudinal axis 41. The slots 58 are configured and dimensioned to receive a pair of pins 60 (only one of the pins 60 being visible in FIGS. 7-9) affixed to the impact rod 44 and the impact block 46 so as to interconnect the impact rod 44 and the impact block 46.

The sleeve 42 can comprise elastic clamping tongs (not shown) at its front end 54. The elastic clamping tongs can be configured and dimensioned to be inserted into the central hole 31 of the plate 20 and to resiliently grip the plate 13 so that the plate 13 can be releasably fixed to the sleeve 42. Alternatively, the front end 54 of the sleeve 42 can be configured to be received in the central hole 31, as best illustrated in FIG. 7, so that the plate 13 can be releasably attached to the front end 54 of the sleeve 42 by an interference fit, or the front end 54 of the sleeve 42 can be conically configured so that a plate 13 having a corresponding conically configured central hole 31 can be frictionally engaged with the front end 54 of the sleeve 42.

The impact rod 44 of the instrument 40 has a leading end 64, a trailing end 66, and an impact head 68 arranged at the trailing end 66. When the impact rod 44 is drawn backward in the sleeve 42 into the retracted position, the trailing end 66 of the impact rod 44 protrudes from the rear end 56 of the sleeve 42 and the leading end 64 of the impact rod 44 is located within the sleeve 42. The impact head 68 is configured and dimensioned to be impinged on by hammer strokes during insertion of the staple 12 into the bone.

Near the front end 54 of the sleeve 42, the impact block 46 is coaxially slideably arranged about the sleeve 42. As best shown in FIG. 7, the central opening 17 of the staple 12 is sized and configured so that the staple 12 can be positioned on the sleeve 42 a distance from the front end 54 of the sleeve 42 with the central opening 17 slidingly receiving the sleeve 42 so that the staple 12 is releasably attached to sleeve 42 by an interference fit. Alternatively, the impact block 46 can comprise elastic clamping tongs (not shown) at its forward end. The elastic clamping tongs can be configured and dimensioned to resiliently grip the bridge 16 of the staple 12 so that the staple 12 can be releasably fixed to the impact block 46. Alternatively, a forward end 70 of the impact block 46 can have a recess which is slightly smaller dimensioned than the peripheral surface of the bridge 16 of the staple 12 so that the staple 12 can be releasably attached to the forward end 70 of the impact block 46 by an interference fit.

As mentioned above, the impact block 46 is connected to the impact rod 44 by the pins 60. The pins 60 are fixed to the impact rod 44 at the leading end 64 of the impact rod 44 and each extends through one of the two slots 58 in the sleeve 42. The staple 12 and the plate 13 are positioned coaxially to each other. Due to the pins 60 being guided in the slots 58, the impact block 46 is axially slidable, but non-rotatably displaceable relative to the sleeve 42. The non-rotatable positioning of the impact block 46 relative to the sleeve 42 causes the legs 14 of the staple 12 to penetrate through the plate 13 upon impaction of the staple 12.

Figure 8:
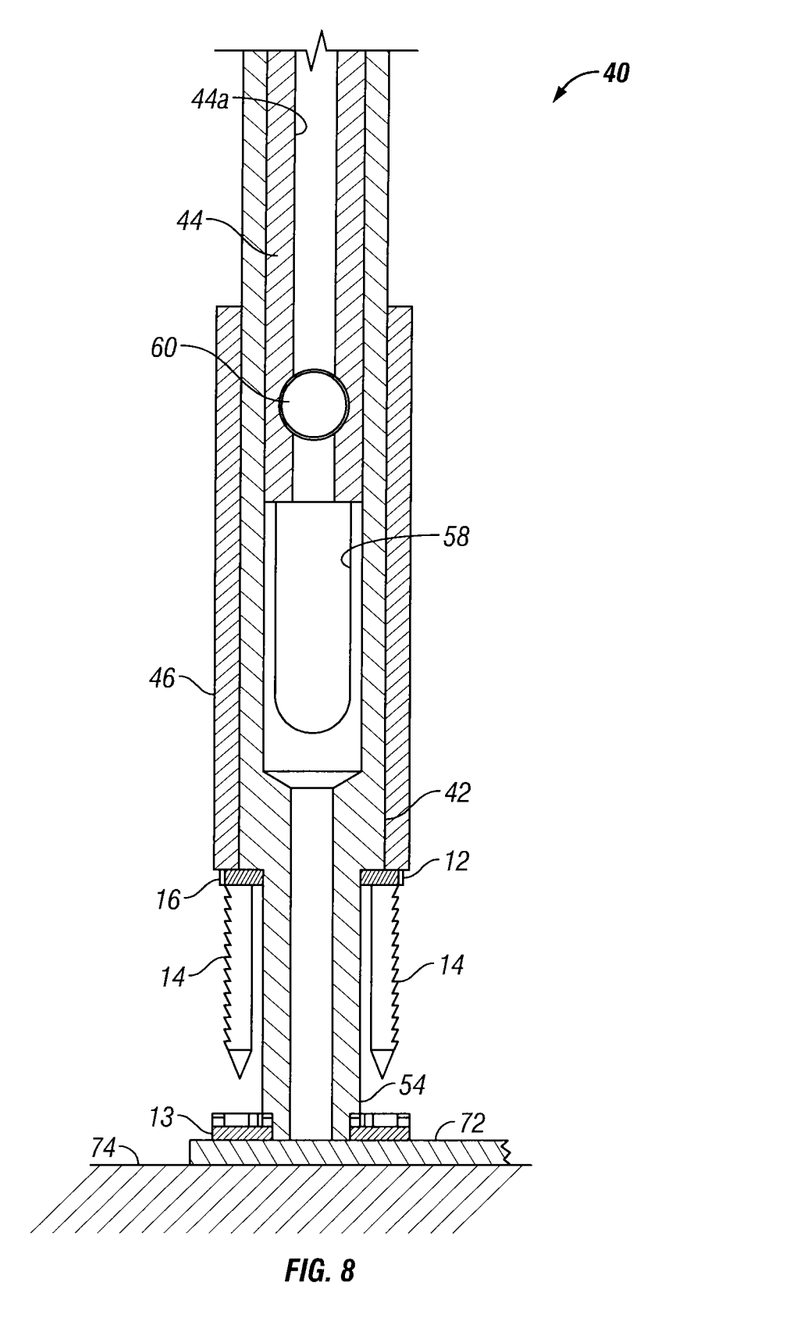
FIG. 8 is a sectional view illustrating the instrument in the retracted position and use of the instrument and the surgical implant to hold soft tissue on a bone surface.
Figure 9:
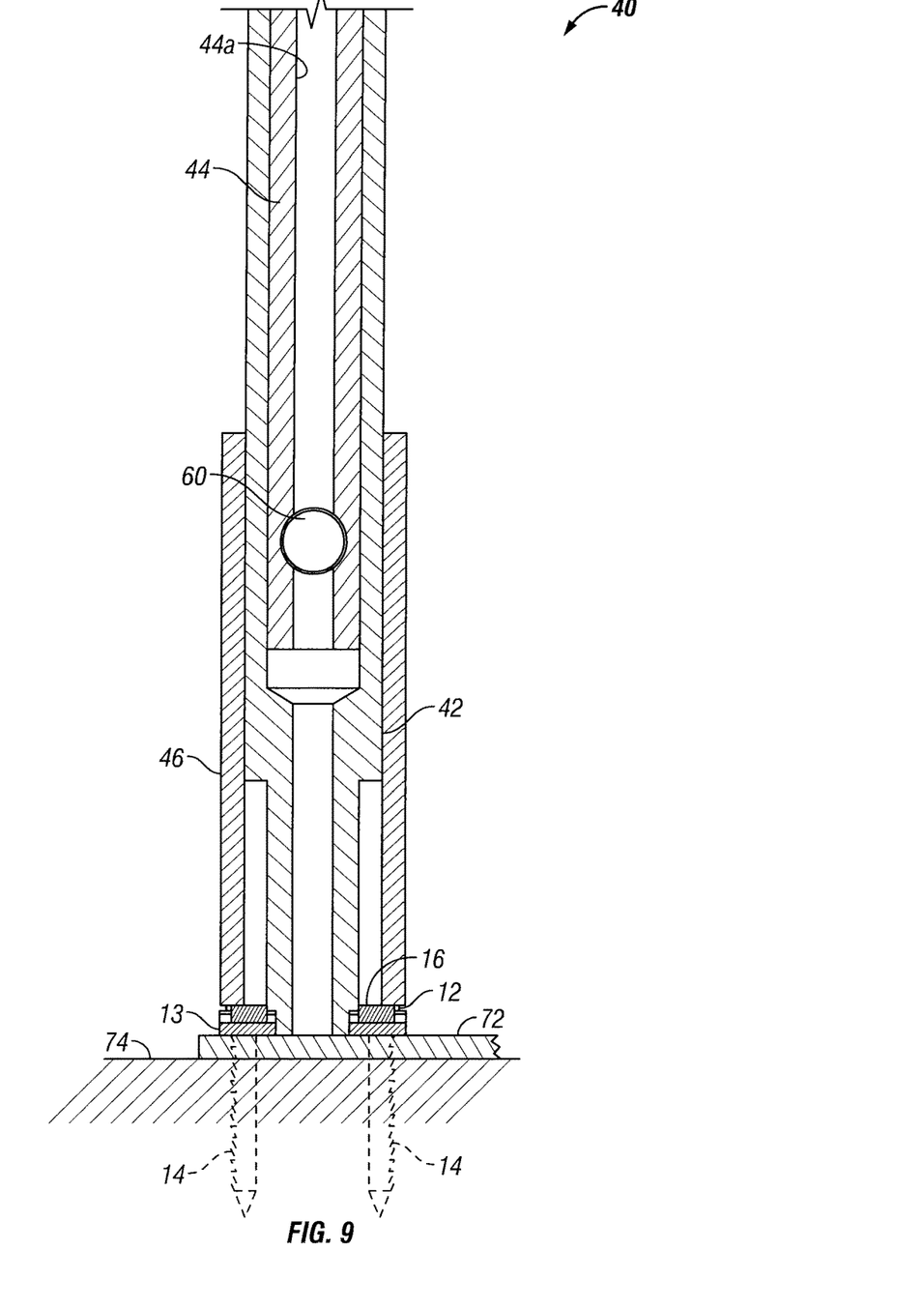
FIG. 9 is a sectional view illustrating the instrument in an extended position with the staple of the surgical implant having been driven through the plate and into the bone to fix the soft tissue to the bone.

Referring now to FIGS. 8 and 9, in use, a combination of the staple 12 and the plate 13 is mounted on the instrument 40. If desired, the instrument 40 can be aligned with a desired fixation point with a Kirschner wire disposed through the passageway 44a of the instrument 40. With the plate 13 attached to the front of the instrument 40, a soft tissue 72 (FIG. 8) may be provisionally blocked or held against a bone 74 with the plate 13 by pressing the lower side of the plate 12 against the soft tissue 72. The staple 12 may then be impacted by hammering on the impact head 68 so as to move the staple 12 along the sleeve 42 and drive the legs 14 of the staple 12 through the plate 13 and into the bone 74 so that the legs 14 of the staple 12 are fixed to the bone 74 with the soft tissue 72 positioned between the plate 13 and the bone 74 and the plate 13 positioned between the bridge 16 of the staple 12 and the soft tissue 72 (FIG. 9). The instrument 40 may then be retracted thereby releasing the staple 12 and the plate 13 from the instrument.

The following applications of the surgical implants disclosed herein are feasible: knee region—collateral ligament reconstruction and patellar tendon repair; shoulder region—rotator cuff repair, biceps tenodesis, coraco-clavicular ligament repair, AC joint separation reduction, and deltoid tears repair; foot region—Achilles tendon repair; and general surgery—small bone ligamentoplasty, mini-open, open and arthroscopic procedures are possible.

From the above description, it is clear that the inventive concepts disclosed and claimed herein are well adapted to carry out the objects and to attain the advantages mentioned herein, as well as those inherent in the invention. While several embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. A kit for fixing a soft tissue to a bone of a patient, comprising:
    an instrument comprising:
        a sleeve having a front end, the sleeve defining an inner channel and having an outer peripheral surface, wherein the inner channel is radially inward of the outer peripheral surface;
        an impact rod slideably arranged in the inner channel of the sleeve; and
        an impact block that is affixed to the impact rod and slideably arranged on the outer peripheral surface of the sleeve;
    at least one staple having a bridge and a plurality of legs extending from the bridge, the bridge having a central opening extending through the bridge such that the staple is positionable on the sleeve of the instrument such that the bridge is spaced apart a distance from the front end of the sleeve and in alignment with the impact block so that impacting the impact rod causes the impact block to contact the bridge of the staple and drive the staple along the sleeve toward the front end of the sleeve; and
    at least one plate having an upper side and a lower side, the plate being positionable on the front end of the sleeve so as to be separated from the staple when the staple is positioned on the sleeve prior to contacting the bridge of the staple with the impact block and in such a way that the plate may be manipulated with the instrument to hold the soft tissue against the bone and in such a way that the staple is fixable to the bone with the plate positioned between the bridge of the staple and the soft tissue when the legs of the staple are driven through the plate and into the bone.

2. The kit of claim 1 wherein the plate has a central opening configured to receive the front end of the sleeve.

3. The kit of claim 1, wherein the staple comprises a material having a tensile strength TS1 and wherein the plate comprises a material having a tensile strength TS2 which is less than the tensile strength TS1 of the staple so that the legs of the staple can penetrate through the plate.

4. The kit of claim 1, wherein the upper side of the plate has a recess configured to matingly receive the bridge of the staple with the legs positioned through the plate.

5. The kit of claim 4, wherein the plate has a central axis orthogonal to the lower side and wherein the plate further comprises one or more channels that are open towards the upper side of the plate and extend across the plate orthogonally to the central axis intersecting the recess of the plate.

6. The kit of claim 4, wherein the bridge of the staple is substantially square shaped with four corners and wherein one leg extends from each of the corners.

7. The kit of claim 4, wherein the bridge of the staple is substantially circularly shaped and wherein the staple includes at least four legs extending from the bridge and being equally spaced about the bridge.

8. The kit of claim 1 wherein the plate has a plurality of blind holes alignable with the legs of the staple when the staple and the plate are positioned on the sleeve.

9. The kit of claim 1 wherein the plate has a plurality of perforations alignable with the legs of the staple when the staple and the plate are positioned on the sleeve.

10. The kit of claim 1, wherein the impact rod has a passageway extending longitudinally therethrough.

* * * * *